(12) United States Patent
Gettman (10) Patent No.: US 9,241,717 B2
(45) Date of Patent: Jan. 26, 2016

(54) ADJUSTABLE FASTENING OR CONSTRICTING DEVICES

(75) Inventor: Matthew T. Gettman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 232 days.

(21) Appl. No.: 13/981,550

(22) PCT Filed: Feb. 3, 2012

(86) PCT No.: PCT/US2012/023835
§ 371 (c)(1),
(2), (4) Date: Jul. 24, 2013

(87) PCT Pub. No.: WO2012/106638
PCT Pub. Date: Aug. 9, 2012

(65) Prior Publication Data
US 2013/0338681 A1 Dec. 19, 2013

Related U.S. Application Data

(60) Provisional application No. 61/439,184, filed on Feb. 3, 2011.

(51) Int. Cl.
*A61B 17/08* (2006.01)
*A61B 17/12* (2006.01)
*A61B 17/122* (2006.01)

(52) U.S. Cl.
CPC ......... *A61B 17/12013* (2013.01); *A61B 17/122* (2013.01); *A61B 17/12009* (2013.01); *A61B 2017/12018* (2013.01); *Y10T 24/4691* (2015.01)

(58) Field of Classification Search
CPC ............... A61B 17/12009; A61B 17/12013; A61B 17/122; A61B 2017/12018; A61B 17/12; A61B 17/12113
USPC .......................... 606/158, 203, 232; 24/711.1
See application file for complete search history.

(56) References Cited

U.S. PATENT DOCUMENTS

| | | | |
|---|---|---|---|
| 5,370,662 A * | 12/1994 | Stone et al. | 606/232 |
| 2004/0030354 A1 * | 2/2004 | Leung et al. | 606/232 |
| 2004/0039404 A1 | 2/2004 | Dreyfuss | |
| 2005/0055027 A1 | 3/2005 | Yeung et al. | |
| 2008/0262534 A1 | 10/2008 | O'Neil | |
| 2009/0192529 A1 | 7/2009 | Kaveney | |
| 2009/0281568 A1 | 11/2009 | Cendan et al. | |

FOREIGN PATENT DOCUMENTS

EP   2 221 008 A2 *   8/2010

OTHER PUBLICATIONS

International Search Report and Written Opinion in International Application No. PCT/US2012/023835, mailed Jul. 30, 2012, 10 pages.
International Preliminary Report on Patentability in International Application No. PCT/US2012/023835, mailed Aug. 15, 2013, 6 pages.
Ganpule et al., "Hem-o-Lok clip eroding into the urethra following laparoscopic radical prostatectomy: A case report and review of literature," Indian J. Urol., Oct.-Dec. 2010, 26(4):580-581.
Weck Hem-o-Lok Ligation System—Safety without compromise, Teleflex, Catalogue, Mar. 2011, 6 pages.

* cited by examiner

*Primary Examiner* — Katherine M Shi
(74) *Attorney, Agent, or Firm* — Fish & Richardson P.C.

(57) ABSTRACT

This document relates to methods and materials involved in fastening or constricting. For example, devices (e.g., adjustable vascular pedicle constricting devices) configured to allow a user (e.g., a surgeon) to apply a band element at least partially around a desired structure (e.g., tissue such as a vascular pedicle) in a manner that allows the degree of constriction to be adjustable are provided.

30 Claims, 12 Drawing Sheets

ADJUSTABLE FASTENING OR CONSTRICTING DEVICES

CROSS-REFERENCE TO RELATED APPLICATIONS

This application is a National Stage application under 35 U.S.C. 371 of International Application No. PCT/US2012/023835, having an International Filing Date of Feb. 3, 2012, which claims the benefit of U.S. Provisional Application Ser. No. 61/439,184, filed Feb. 3, 2011. The disclosure of the prior application is considered part of (and is incorporated by reference in) the disclosure of this application.

BACKGROUND

1. Technical Field

This document relates to methods and materials involved in fastening or constricting. For example, this document relates to devices (e.g., adjustable and/or removable devices such as adjustable vascular pedicle constricting devices) configured to allow a user (e.g., a surgeon) to apply a band element at least partially around a desired structure (e.g., tissue such as a vascular pedicle) in a manner that allows the degree of constriction to be adjustable.

2. Background Information

Surgeons perform many different types of surgeries using procedures ranging from open surgery to minimally invasive surgery (e.g., laparoscopic and endoscopic surgeries). In some cases, a surgeon may need to fasten two tissues together, hold a particular tissue in a desired position, or constrict a particular tissue (e.g., a vascular pedicle). In such cases, a surgeon can use surgical sutures or surgical clips.

SUMMARY

This document provides methods and materials involved in fastening or constricting items. For example, this document provides devices (e.g., adjustable vascular pedicle constricting devices) configured to allow a user (e.g., a surgeon) to apply a band element at least partially around a desired structure (e.g., tissue such as a vascular pedicle) in a manner that allows the degree of constriction to be adjustable. The methods and materials provided herein can be used in the medical setting and non-medical setting. For example, the methods and materials provided herein can be used in the medical setting to fasten two or more tissues together, to hold or hang a particular tissue in a desired position, or to constrict a particular tissue (e.g., a vascular pedicle or vas deferens). In some cases, the devices provided herein can be used as tourniquet-type devices in, for example, trauma settings or in the management of erectile dysfunction (e.g., as a penile constriction band). In some cases, the methods and materials provided herein can be used in the non-medical setting to fasten two or more items together, to hold or hang a particular item in a desired position (e.g. a pipe, conduit, wire, or picture frame), or to constrict a particular item (e.g., a hose or tubing). For example, the devices provided herein can be used as a key chain, a hair holder, as a mechanism to hang a curtain or drape, or as a mechanism to secure a tarp, sail, or protective cover.

In general, one aspect of this document features a device comprising, or consisting essentially of, a pin element, a band element attached to the pin element, and a ring element attached to the band element, wherein the pin element comprises a shaft portion having a proximal end, a distal end, and an axis extending from the proximal end to the distal end, wherein the shaft portion comprises a locking structure and a protrusion, wherein the ring element is configured to be advanced over the distal end along the axis toward the proximal end and is configured to engage the locking structure, wherein the ring element is configured to rotate with respect to the pin element in a first direction, and wherein the ring element is configured to interact with the protrusion in a manner that restricts rotation of the ring element with respect to the pin element in a direction opposite the first direction. The pin element can comprise a pointed distal end region. The pin element can be compressible. Compression of the pin element can release the ring element from the locking structure such that the ring element is removable from the pin element. The pin element can comprise a band holding region. The band holding region can be at a proximal end region of the pin element. The pin element can comprise two or more locking structures. The pin element can comprise two or more protrusions. The pin element can comprise a hollow central region along the axis. The pin element can comprise a blunt distal end. The ring element can comprise a continuous ring structure. The ring element can comprise an inner surface comprising a ratcheting structure configured to engage the protrusions. The ring element can comprise a band holding region. The band element can comprise a protrusion. The protrusion of the band element can be a spike-like structure. The band element can comprise two or more protrusions.

In another aspect, this document features a method for using a device to constrict vascular tissue. The device comprises, or consists essentially of, a pin element, a band element attached to the pin element, and a ring element attached to the band element, wherein the pin element comprises a shaft portion having a proximal end, a distal end, and an axis extending from the proximal end to the distal end, wherein the shaft portion comprises a locking structure and a protrusion, wherein the ring element is configured to be advanced over the distal end along the axis toward the proximal end and is configured to engage the locking structure, wherein the ring element is configured to rotate with respect to the pin element in a first direction, and wherein the ring element is configured to interact with the protrusion in a manner that restricts rotation of the ring element with respect to the pin element in a direction opposite the first direction. The method comprises, or consists essentially of, (a) positioning the pin element in proximity with the vascular tissue, (b) positioning the ring element around the vascular tissue such that the band element is positioned at least partially about the vascular tissue, (c) advancing the ring element over the distal end and along the axis toward the proximal end to a position wherein the ring element engages the locking structure and a closed loop is formed at least partially around the vascular tissue, and (d) rotating the ring element in the first direction to shorten the free length of the band element, thereby applying the desired amount of constriction to the vascular tissue.

In another aspect, this document features a device for deploying a fastening device. The device comprises, or consists essentially of, a handle structure and an attachment pin configured to engage the fastening device, wherein the device is configured to prevent the fastening device from being deployed with slippage during a laparoscopic or robotic surgery. The fastening device can comprise a pin element, a band element attached to the pin element, and a ring element attached to the band element, wherein the pin element comprises a shaft portion having a proximal end, a distal end, and an axis extending from the proximal end to the distal end, wherein the shaft portion comprises a locking structure and a protrusion, wherein the ring element is configured to be advanced over the distal end along the axis toward the proximal end and is configured to engage the locking structure, wherein the ring element is configured to rotate with respect to the pin element in a first direction, and wherein the ring element is configured to interact with the protrusion in a manner that restricts rotation of the ring element with respect to the pin element in a direction opposite the first direction.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials that can be used to fasten or constrict one or more items. For example, this document provides devices having a pin element, a band element, and a ring element. In general, a pin element can be attached to a band element, which can be attached to a ring element. In addition, the pin element can be configured to receive the ring element. For example, a ring element can have a continuous ring configuration with a center opening sized and shaped to allow the ring element to slide over a distal end region of a pin element. Once positioned over a portion of the pin element, the ring element, the pin element, or both can be rotated such that at least a portion of the band element winds around the ring element, the pin element, or both, thereby shortening the length of the free, unwound portion of the band element. Thus, the amount of rotation that is used can control the size of the opening defined by the device. For example, little or no rotation can be used to maintain a large opening, while more rotation can be used to reduce the size of the opening. Reducing the size of the opening defined by the device by rotating the ring element, the pin element, or both can allow increasing levels of constriction to be applied to the items within the opening. For example, blood vessels within the opening defined by the device once the ring element is positioned over at least a portion of the pin element can be constricted in a manner the restricts blood flow by rotating the ring element, the pin element, or both to the desired level of tightness.

The devices provided herein can be configured such that the ring element secures onto the pin element in a manner having a reduced chance of accidentally disengaging. For example, the pin element and ring element can have mating structures capable of locking the ring element onto the pin element to avoid accidental disengagement. In some cases, the device can be configured such that the ring element is removable, when desired, from the pin element. For example, a device provided herein can have a pin element that is compressible such that the locking mechanism configured to secure the ring element onto the pin element can be disengaged, thereby allowing the ring element to be separated from the pin element.

Figure 1:
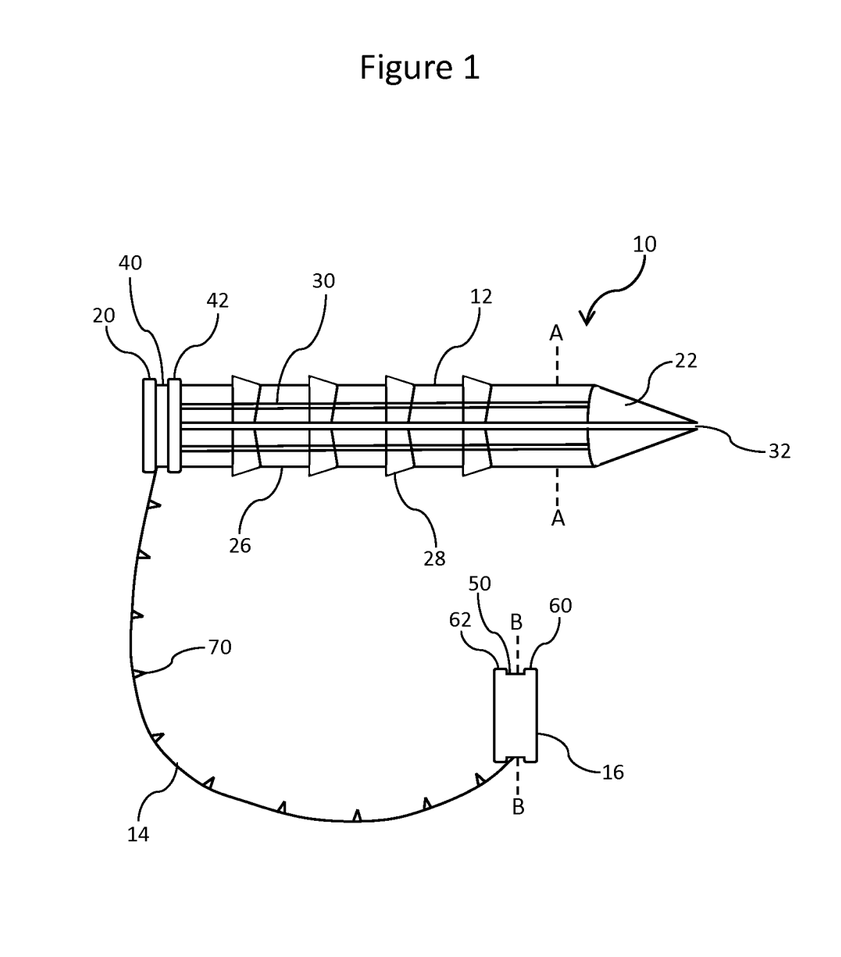
FIG. 1 is a side view of an exemplary device for fastening or constricting one or more items.

With respect to FIG. 1, device 10 can include a pin element 12, a band element 14, and a ring element 16. Pin element 12 can have a proximal end region 20 and a distal end region 22. Proximal end region 20 can include a point of attachment for band element 14, which can be attached to ring element 16. In some cases, the distal end region 22 of pin element 12 can be configured to be pointed, curved, rounded, or blunt. For example, when device 10 is designed to constrict tissue such as a vascular pedicle, the distal end region 22 can be pointed to a degree such that pin element 12 can be advanced through at least a portion of tissue using, for example, a variety of deployment strategies and devices. When device 10 is designed to fasten two items such as two hoses or tubes, the distal end region 22 can be blunt or rounded such that a person handling the fastened items is not injured by any sharp edges of the device. In some cases, when device 10 is designed to be used during a surgical procedure, the distal end region 22 can be blunt or rounded such that nearby tissues are not injured by any sharp edges of the device. In some cases, device 10 can be short, and region 22 can be modified to permit device 10 to be attached to a wall or other structure. In such cases, device 10 can have a modification of end region 22 to potentially accept a deployment tool and/or permit deployment by a screw-type motion or other means.

Figure 2A:
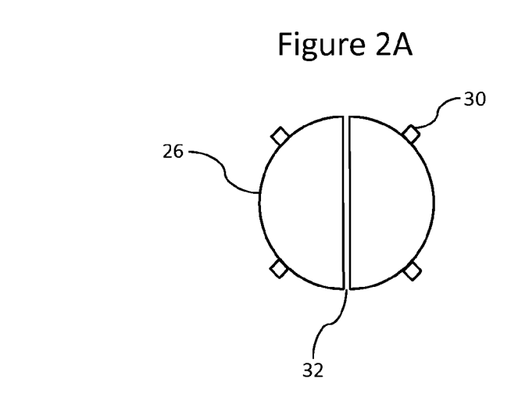
FIG. 2A is a cross section view of the device of FIG. 1 along the A-A line depicting an exemplary internal configuration.
Figure 2B:
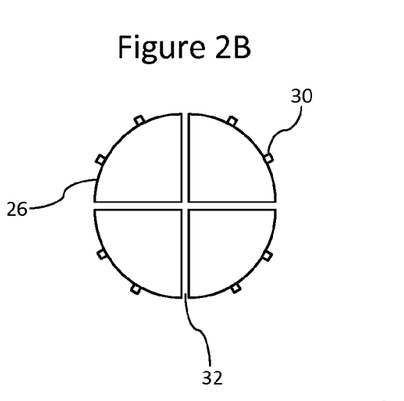
FIG. 2B is a cross section view of the device of FIG. 1 along the A-A line depicting an exemplary internal configuration.
Figure 2C:
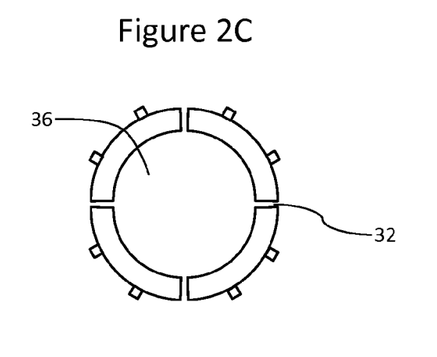
FIG. 2C is a cross section view of the device of FIG. 1 along the A-A line depicting an exemplary internal configuration.

Pin element 12 can include a shaft portion 26. Shaft portion 26 can include one or more locking elements 28. Locking elements 28 can be configured such that ring element 16 can be advanced forward over the distal end region 22 of pin element 12 in a direction toward proximal end region 20 and such that ring element 16 is restricted from moving backwards in a manner that would result in the ring element 16 being removed from the pin element 12. In some cases, pin element 12 can be configured to have one or more openings 32 (e.g., slits) that can allow the cross sectional diameter or perimeter of pin element 12 to be compressed. Compression of the cross sectional diameter or perimeter of pin element 12 by, for example, pressure applied by a human's fingers can remove the restrictive nature of locking elements 28, thereby allowing ring element 16 to be removed from pin element 12. With reference to FIGS. 2A and 2B, device 10 can include opening 32, which can extend across shaft portion 26 in one or more directions. In some cases, a center region of shaft portion 26 can be hollow, thereby defining a hollow opening 36 as shown in FIG. 2C. Hollow opening 36 can extend the entire length of shaft portion 26 or a portion thereof. For example, hollow opening 36 can extend from distal end region 22 along shaft portion 26 just past the final locking element 28. Opening 36 can include a modification configured to permit the device to be fixed to another structure. For example, the device can include an opening for a nail, screw, or other support structure.

Pin element 12 can be constructed from any appropriate material or combination of materials. Examples of materials that can be used to make pin element 12 include, without limitation, plastic, biodegradable polymer, metal, wood, and vulcanized rubber. In some cases, pin element 12 can be constructed from a flexible material such as vulcanized rubber, plastic, or polymer. Flexible materials can be used when the particular application requires an increased ease of removing ring element 16 from pin element 12. Such applications may have fewer concerns about an accidental release of ring element 16 from pin element 12. In some cases, pin element 12 can be constructed from a rigid material such as plastic, metal, wood, or other material. Rigid materials can be used when the particular application requires an increased need to minimize accidental release of ring element 16 from pin element 12. Such applications may have fewer concerns about the need for an increased ease of removing ring element 16 from pin element 12.

Pin element 12 can have any appropriate cross sectional shape such as a circular, oval, rectangular, triangular, or other shape that may have application. Typically, the length of pin element 12 can range from about 0.5 cm to about 10 cm (e.g., from about 0.5 cm to about 5 cm, from about 0.5 cm to about 2.5 cm, from about 1 cm to about 5 cm, from about 1 cm to about 2.5 cm, or from about 1 cm to about 1.5 cm) for medical applications. For nonmedical applications, lengths of up to 5 cm or more can be used (e.g., from about 2 cm to about 50 cm, from about 2 cm to about 40 cm, from about 2 cm to about 30 cm, from about 2 cm to about 20 cm, from about 2 cm to about 10 cm, from about 2 cm to about 5 cm, from about 5 cm to about 25 cm, from about 5 cm to about 20 cm, or from about 5 cm to about 15 cm). The width of pin element 12 can range from about 0.2 cm to about 5 cm (e.g., from about 0.3 to about 5 cm, from about 0.5 to about 5 cm, from about 1.5 to about 5 cm, from about 0.5 to about 4 cm, from about 0.5 to about 3 cm, or from about 0.5 to about 2.5 cm) depending on application. Ring element 16 can have a continuous or partial ring configuration that defines an opening or space sized and shaped to allow ring element 16 to slide over distal end region 22 and releasably engage a locking element 28 of shaft portion 26. The opening or space defined by ring element 16 can be any appropriate shape provided that it can releasably mate with shaft portion 26. Examples of such shapes include, without limitation, circular or oval shapes.

Pin element 12 can include one or more protrusions 30. Protrusions 30 can extend axially along the entire length or a portion of the length of shaft portion 26. In some cases, protrusions 30 can be extend over locking elements 28 or can be discontinuous in the areas that include locking elements 28. Protrusions 30 can be configured to interact with corresponding protrusions 52 (e.g., ratchets) located on an inner surface of ring element 16. The interaction between protrusions 30 of pin element 12 and protrusions 52 of ring element 16 can be such that ring element 16 is free to rotate in one direction (e.g., clock-wise) with respect to pin element 12 and is not free to rotate in the opposite direction (e.g., counter clock-wise) with respect to pin element 12. In some cases, compression of pin element 12 can release the interaction between protrusions 30 and protrusions 52 such that ring element 16 is free to rotate about pin element 12 in both directions. This can allow the device to be released or removed.

In some cases, a device provided herein can include a pin element 312 and a ring element 316 as shown in FIGS. 10A-E. In such cases, ring element 316 can include protrusions 352 that interact with openings 336 of pin element 312 (see, e.g., FIG. 10E). A device having a pin element 312 and a ring element 316 as shown in FIGS. 10A-E can include a band element (not shown in FIGS. 10A-E) as described herein.

Figure 3:
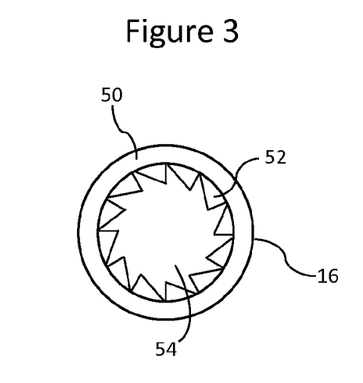
FIG. 3 is a cross section view of the device of FIG. 1 along the B-B line.

Rotation of ring element 16 with respect to pin element 12, rotation of pin element 12 with respect to ring element 16, or rotation of both can be designed to wrap at least a portion of band element 14 around a portion of ring element 16, pin element 12, or both. For example, in some cases, rotation of pin element 12 can result in at least a portion of band element 14 wrapping around a band holding region 40 of pin element 12. Band holding region 40 can be defined by a bulged region at proximal end 20 and a bulged region 42. In some cases, rotation of ring element 16 can result in at least a portion of band element 14 wrapping around a band holding region 50 of ring element 16 (FIG. 3). Band holding region 50 can be defined by bulged region 60 and 62.

Band element 14 can be configured to provide a flexible and adjustable connection between pin element 12 and ring element 16 such that attachment of ring element 16 over the distal end region of pin element 12 results in the device forming a closed loop structure. The closed loop structure can be used to fasten two or more items together, can be used to hold or position one or more items in a particular location or configuration, can be used to provide constrictive pressure against one or more items, or can hang one or more items.

Band element 14 can have a length, width, and thickness designed to achieve the desired fastening and/or constricting goals. For example, a device provided herein designed to constrict a vascular pedicle can have a length of about 3 cm to about 5 cm, a width of about 2 mm to about 10 mm, and a thickness of about 2 mm to about 10 mm. A device provided herein designed to hold keys (e.g., house or car keys) can have a length of about 3 cm to about 10 cm, a width of about 4 mm to about 10 mm, and a thickness of about 3 mm to about 10 mm. A device provided herein designed to act as a hanger can have a length of about 3 cm to about 15 cm, a width of about 3 mm to about 5 cm, and a thickness of about 3 mm to about 10 mm. As described herein the length of band element 14 can be shortened during use by rotating ring element 16 relative to pin element 12, by rotating pin element 12 relative to ring element 16, or by rotating both. Depending on the desired application, band element 14 can have varying degrees of thickness or particular characteristics (e.g., width distensibility) to achieve the intended goal.

Figure 7A:
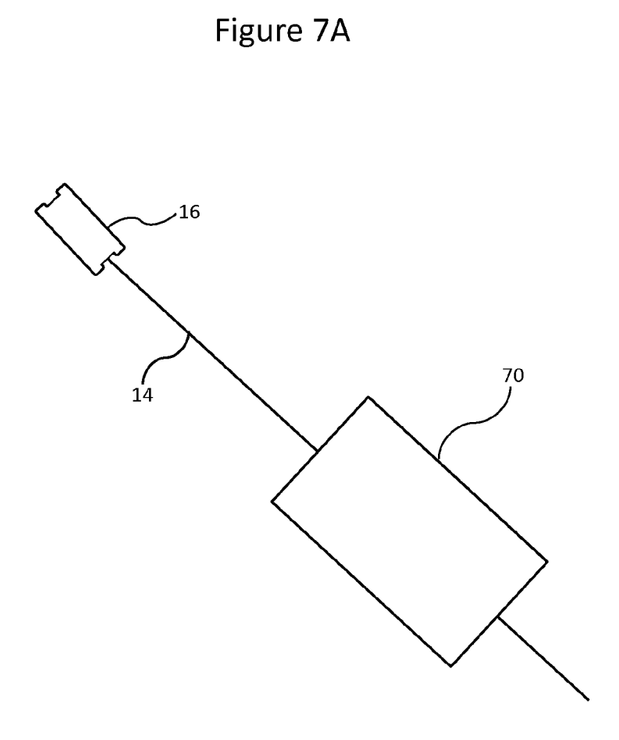
FIG. 7A is a side view of one example of a band element attached to a ring element.
Figure 7B:
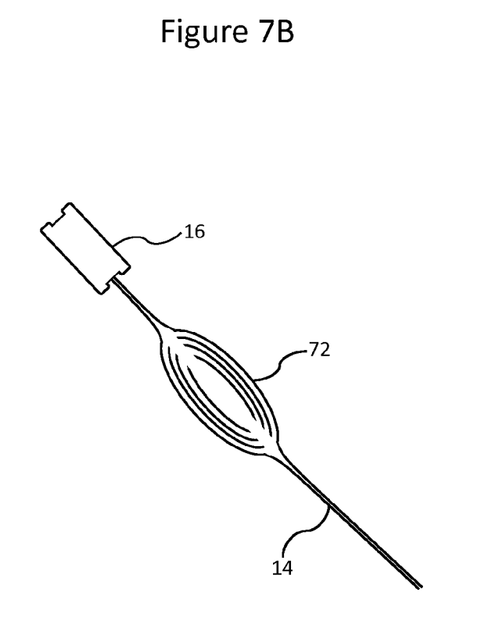
FIG. 7B is a side view of another example of a band element attached to a ring element.
Figure 7C:
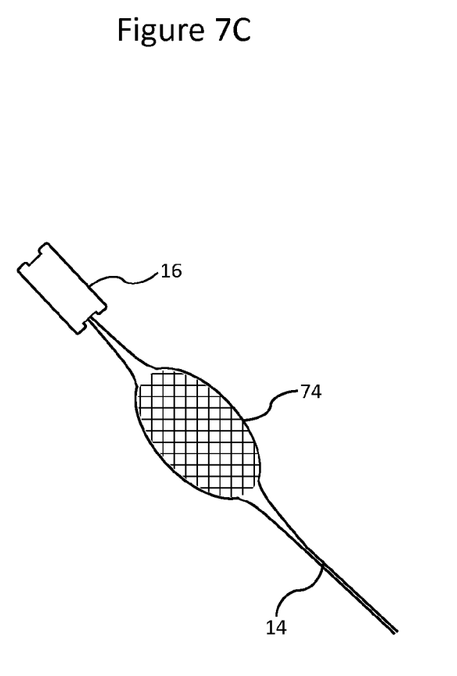
FIG. 7C is a side view of another example of a band element attached to a ring element.
Figure 7D:
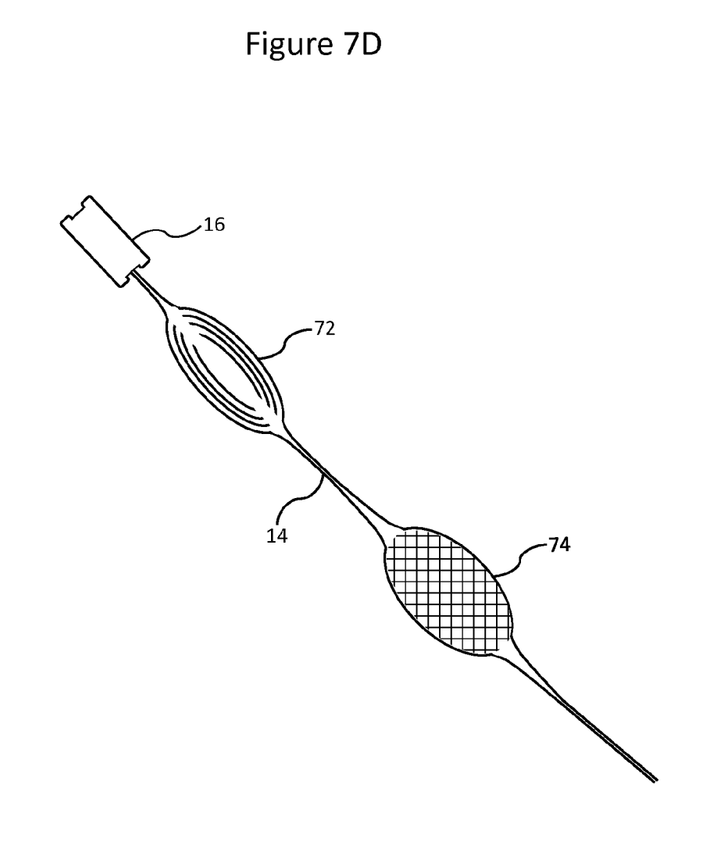
FIG. 7D is a side view of another example of a band element attached to a ring element.

With reference to FIG. 7A, band element 14 can be configured to have an enlarged area 70. Enlarged area 70 can be any appropriate shape including, without limitation, rectangular, square, oval, circular, triangular, polygonal, and irregular shapes. In some cases, an enlarged area can be a distensible widened area 72 as shown, for example, in FIG. 7B. In some cases, an enlarged area can included an enlarged mesh area 74 as shown, for example, in FIG. 7C. In some cases, a band element can include multiple enlarged areas (e.g., two, three, four, five, six, seven eight, nine, ten, or more enlarged areas). For example, a band element can have a distensible widened area 72 and an enlarged mesh area 74 as shown, for example, in FIG. 7D.

In some cases, band element 14 can contain one or more structures 70. Structures 70 can be designed to facilitate a desired level of interaction between band element 14 and the one or more items within the closed loop of the device. For example, in some cases, structures 70 can be spike-like structures configured to provide at least some gripping capability of the band element to a tissue being constricted by the device. Examples of other structures that can be attached to or part of band element 14 include, without limitation, decorative elements, jewels, lights, sensors, and receiving/transmitting devices.

Figure 4:
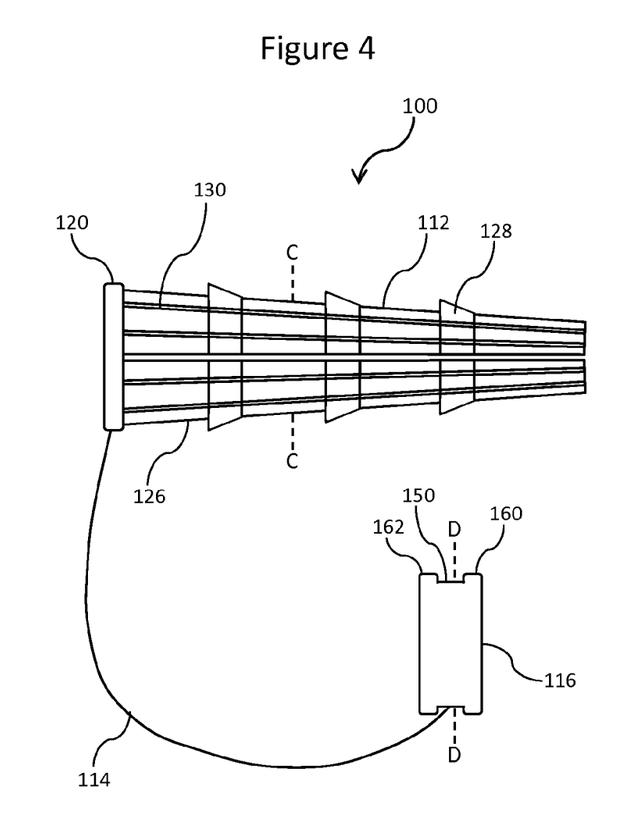
FIG. 4 is a side view of an exemplary device for fastening or constricting one or more items.

With respect to FIG. 4, device 100 can include a pin element 112, a band element 114, and a ring element 116. Pin element 112 can have a proximal end region 120 and a distal end region. Proximal end region 120 can include a point of attachment for band element 114, which can be attached to ring element 116. In some cases, the distal end region of pin element 112 can be configured to be pointed, curved, rounded, or blunt. For example, when device 110 is designed to constrict tissue such as a vascular pedicle, the distal end region can be pointed to a degree such that pin element 112 can be advanced through at least a portion of tissue. When device 100 is designed to fasten two items such as two hoses or tubes, the distal end region can be blunt or rounded such that a person handling the fastened items is not injured by any sharp edges of the device. In some cases, when device 100 is designed to be used during a surgical procedure, the distal end region can be blunt or rounded such that nearby tissues are not injured by any sharp edges of the device.

Figure 5A:
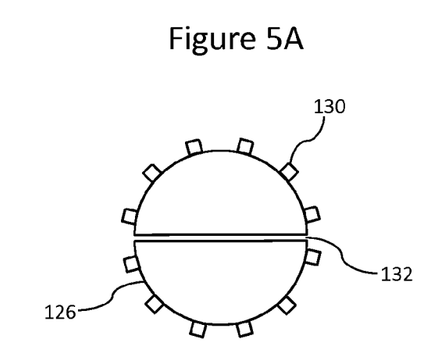
FIG. 5A is a cross section view of the device of FIG. 1 along the C-C line depicting an exemplary internal configuration.
Figure 5B:
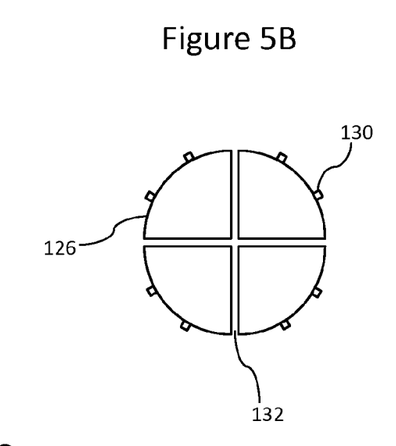
FIG. 5B is a cross section view of the device of FIG. 1 along the C-C line depicting an exemplary internal configuration.
Figure 5C:
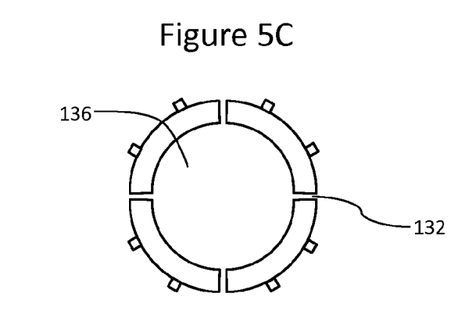
FIG. 5C is a cross section view of the device of FIG. 1 along the C-C line depicting an exemplary internal configuration.

Pin element 112 can include a shaft portion 126. Shaft portion 126 can be tapered. For example, shaft portion 126 can taper in its diameter or perimeter in a direction from the proximal end region 120 toward the distal end region. In some cases, shaft portion 112 can include one or more locking elements 128. Locking elements 128 can be configured such that ring element 116 can be advanced forward over the distal end region of pin element 112 in a direction toward proximal end region 120 and such that ring element 116 is restricted from moving backwards in a manner that would result in ring element 116 being removed from pin element 112. In some cases, pin element 112 can be configured to have one or more openings 132 (e.g., slits) that can allow the cross sectional diameter or perimeter of pin element 112 to be compressed. Compression of the cross sectional diameter or perimeter of pin element 112 by, for example, pressure applied by a human's fingers can remove the restrictive nature of locking elements 128, thereby allowing ring element 116 to be removed from pin element 112. With reference to FIGS. 5A and 5B, device 100 can include opening 132, which can extend across shaft portion 126 in one or more directions. In some cases, a center region of shaft portion 126 can be hollow, thereby defining a hollow opening 136 as shown in FIG. 5C. Hollow opening 136 can extend the entire length of shaft portion 126 or a portion thereof. For example, hollow opening 136 can extend from a distal end region along shaft portion 126 just past the final locking element 128.

Pin element 112 can be constructed from any appropriate material or combination of materials. Examples of materials that can be used to make pin element 112 include, without limitation, plastic, biodegradable polymer, metal, wood, and vulcanized rubber. In some cases, pin element 112 can be constructed from a flexible material such as vulcanized rubber, plastic, or polymer. Flexible materials can be used when the particular application requires an increased ease of removing ring element 116 from pin element 112. Such applications may have fewer concerns about an accidental release of ring element 116 from pin element 112. In some cases, pin element 112 can be constructed from a rigid material such as plastic, metal, wood, or other material. Rigid materials can be used when the particular application requires an increased need to minimize accidental release of ring element 116 from pin element 112. Such applications may have fewer concerns about the need for an increased ease of removing ring element 116 from pin element 112.

Pin element 112 can have any appropriate cross sectional shape such as a circular, oval, rectangular, triangular, or other shape that may have application. Typically, the length of pin element 112 can range from about 0.5 cm to about 10 cm (e.g., from about 0.5 cm to about 5 cm, from about 0.5 cm to about 2.5 cm, from about 1 cm to about 5 cm, from about 1 cm to about 2.5 cm, or from about 1 cm to about 1.5 cm) for medical applications. For nonmedical applications, lengths of up to 5 cm or more can be used (e.g., from about 2 cm to about 50 cm, from about 2 cm to about 40 cm, from about 2 cm to about 30 cm, from about 2 cm to about 20 cm, from about 2 cm to about 10 cm, from about 2 cm to about 5 cm, from about 5 cm to about 25 cm, from about 5 cm to about 20 cm, or from about 5 cm to about 15 cm). The width of pin element 112 can range from about 0.2 cm to about 5 cm (e.g., from about 0.3 to about 5 cm, from about 0.5 to about 5 cm, from about 1.5 to about 5 cm, from about 0.5 to about 4 cm, from about 0.5 to about 3 cm, or from about 0.5 to about 2.5 cm) depending on application.

Ring element 116 can have a continuous or partial ring configuration that defines an opening or space sized and shaped to allow ring element 116 to slide over distal end region and releasably engage a locking element 128 of shaft portion 126. The opening or space defined by ring element 116 can be any appropriate shape provided that it can releasably mate with shaft portion 126. Examples of such shapes include, without limitation, circular and oval shapes.

Pin element 112 can include one or more protrusions 130. Protrusions 130 can extend axially along the entire length or a portion of the length of shaft portion 126. In some cases, protrusions 130 can be extend over locking elements 130 or can be discontinuous in the areas that include locking elements 130. Protrusions 130 can be configured to interact with corresponding protrusions 152 (e.g., ratchets) located on an inner surface of ring element 116. The interaction between protrusions 130 of pin element 112 and protrusions 152 of ring element 116 can be such that ring element 116 is free to rotate in one direction (e.g., clock-wise) with respect to pin element 112 and is not free to rotate in the opposite direction (e.g., counter clock-wise) with respect to pin element 112. In some cases, compression of pin element 112 can release the interaction between protrusions 130 and protrusions 152 such that ring element 116 is free to rotate about pin element 112 in both directions.

Figure 6:
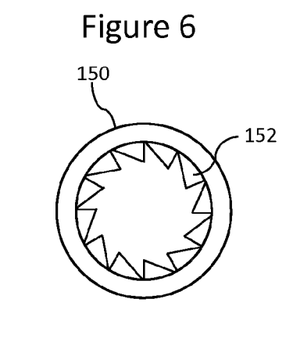
FIG. 6 is a cross section view of the device of FIG. 4 along the D-D line.

Rotation of ring element 116 with respect to pin element 112, rotation of pin element 112 with respect to ring element 116, or rotation of both can be designed to wrap at least a portion of band element 114 around a portion of ring element 116, pin element 112, or both. For example, in some cases, rotation of ring element 116 can result in at least a portion of band element 114 wrapping around a band holding region 150 of ring element 116 (FIG. 6). Band holding region 150 can be defined by bulged region 160 and 162.

Band element 114 can be configured to provide a flexible and adjustable connection between pin element 112 and ring element 116 such that attachment of ring element 116 over the distal end region of pin element 112 results in the device forming a closed loop structure. The closed loop structure can be used to fasten two or more items together, can be used to hold or position one or more items in a particular location or configuration, or can be used to provide constrictive pressure against one or more items.

Band element 114 can have a length, width, and thickness designed to achieve the desired fastening and/or constricting goals as described above for band element 14 (see, e.g., FIGS. 7A-7D).

In some cases, band element 114 can contain one or more structures. Such structures can be designed to facilitate a desired level of interaction between band element 114 and the one or more items within the closed loop of the device. For example, in some cases, structures such as spike-like structures can be configured to provide at least some gripping capability of the band element to a tissue being constricted by the device.

Figures 11, 12:
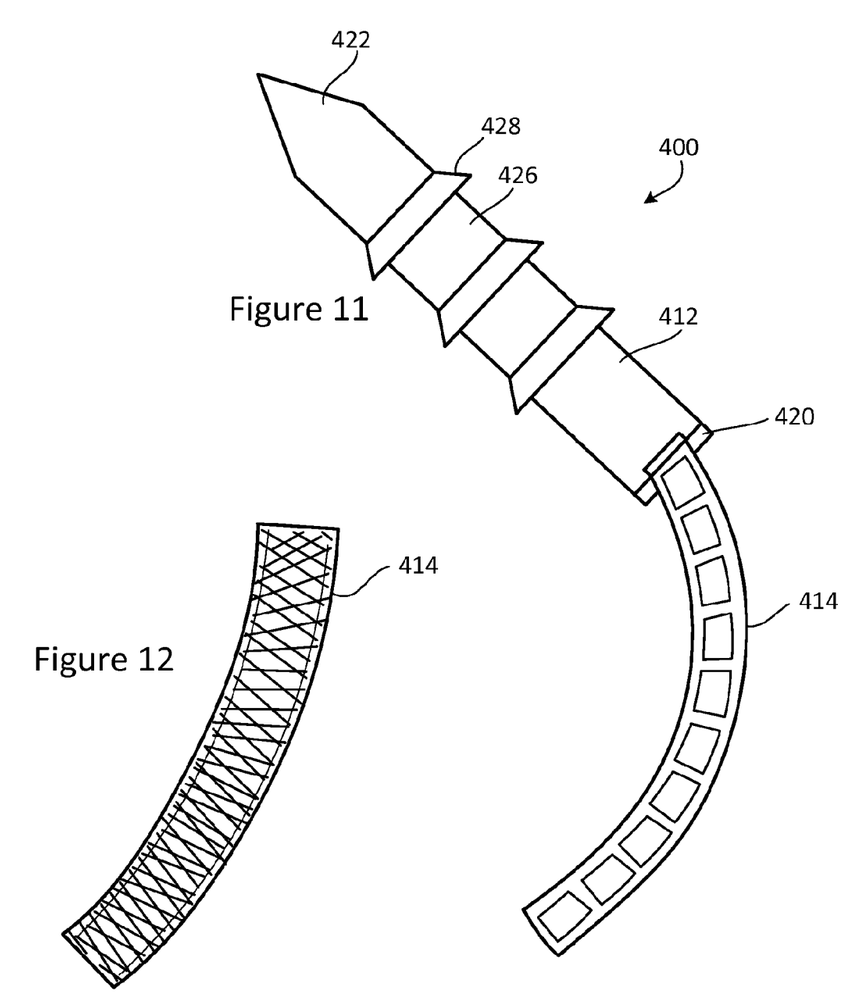
FIG. 11 is a side view of an exemplary device for fastening or constricting one or more items.
FIG. 12 is a side view of a band element in accordance with some embodiments.

With respect to FIG. 11, device 400 can include a pin element 412 and a band element 414. Pin element 412 can have a proximal end region 420 and a distal end region 422. Proximal end region 420 can include a point of attachment for band element 414. In some cases, the distal end region 422 of pin element 412 can be configured to be pointed, curved, rounded, or blunt. For example, when device 400 is designed to constrict tissue such as a vascular pedicle, the distal end region can be pointed to a degree such that pin element 412 can be advanced through at least a portion of tissue. When device 400 is designed to fasten two items such as two hoses or tubes, the distal end region can be blunt or rounded such that a person handling the fastened items is not injured by any sharp edges of the device. In some cases, when device 400 is designed to be used during a surgical procedure, the distal end region 422 can be blunt or rounded such that nearby tissues are not injured by any sharp edges of the device.

Pin element 412 can include a shaft portion 426. Shaft portion 426 can be tapered. For example, shaft portion 426 can taper in its diameter or perimeter in a direction from the proximal end region 420 toward the distal end region 422. In some cases, shaft portion 412 can include one or more locking elements 428. Locking elements 428 can be configured such that band element 414 can be advanced forward over the distal end region 422 of pin element 412 in a direction toward proximal end region 420 and such that band element 414 is restricted from moving backwards in a manner that would result in band element 414 being removed from pin element 412. In some cases, pin element 412 can be configured to be solid.

Pin element 412 can be constructed from any appropriate material or combination of materials. Examples of materials that can be used to make pin element 412 include, without limitation, plastic, biodegradable polymer, metal, wood, and vulcanized rubber. In some cases, pin element 412 can be constructed from a flexible material such as vulcanized rubber, plastic, or polymer. In some cases, pin element 412 can be constructed from a rigid material such as plastic, metal, wood, or other material. Rigid materials can be used when the particular application requires an increased need to minimize accidental release of band element 414 from pin element 12. Such applications may have fewer concerns about the need for an increased ease of removing band element 414 from pin element 112.

Pin element 412 can have any appropriate cross sectional shape such as a circular, oval, rectangular, triangular, or other shape that may have application. Typically, the length of pin element 412 can range from about 0.5 cm to about 10 cm (e.g., from about 0.5 cm to about 5 cm, from about 0.5 cm to about 2.5 cm, from about 1 cm to about 5 cm, from about 1 cm to about 2.5 cm, or from about 1 cm to about 1.5 cm) for medical applications. For nonmedical applications, lengths of up to 5 cm or more can be used (e.g., from about 2 cm to about 50 cm, from about 2 cm to about 40 cm, from about 2 cm to about 30 cm, from about 2 cm to about 20 cm, from about 2 cm to about 10 cm, from about 2 cm to about 5 cm, from about 5 cm to about 25 cm, from about 5 cm to about 20 cm, or from about 5 cm to about 15 cm). The width of pin element 412 can range from about 0.2 cm to about 5 cm (e.g., from about 0.3 to about 5 cm, from about 0.5 to about 5 cm, from about 1.5 to about 5 cm, from about 0.5 to about 4 cm, from about 0.5 to about 3 cm, or from about 0.5 to about 2.5 cm) depending on application.

Band element 414 can be configured to provide a flexible and adjustable connection between pin element 412 and band element 414 such that attachment of band element 414 over the distal end region 422 of pin element 412 results in the device forming a closed loop structure. The closed loop structure can be used to fasten two or more items together, can be used to hold or position one or more items in a particular location or configuration, or can be used to provide constrictive pressure against one or more items.

Band element 414 can have a length, width, and thickness designed to achieve the desired fastening and/or constricting goals as described above for band element 14 or 114 (see, e.g., FIGS. 7A-7D).

In some cases, band element 414 can have a windowed configuration as shown in FIG. 11. In some cases, band element 414 can be configured to have a mesh configuration as shown in FIG. 12.

Figure 13:
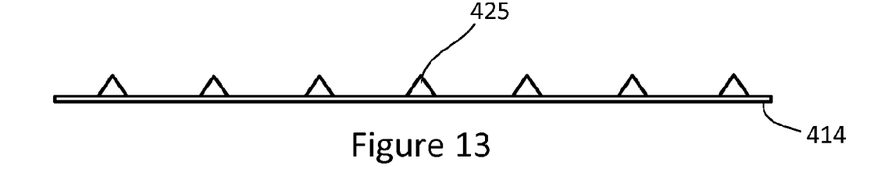
FIG. 13 is a side view of a band element in accordance with some embodiments.

In some cases, band element 414 can contain one or more structures. Such structures can be designed to facilitate a desired level of interaction between band element 414 and the one or more items within the closed loop of the device. For example, in some cases, structures such as spike-like structures (e.g., structures 425 of FIG. 13) can be configured to provide at least some gripping capability of the band element to a tissue being constricted by the device (see, e.g., FIG. 13).

In some cases, a device provided herein can be used to control a vascular pedicle. In such cases, after identifying the tissue to be secured, the tissue can be dissected sufficiently to permit the device to pierce the tissue. In this situation, a pin element of the device can initially pierce the tissue. After the pin element is in place, a ring element of the device can be positioned around the tissue to be occluded and placed on the tip of the pin element. Using downward pressure, the ring element can be snapped closer to the proximal end of the pin element. After sufficient tissue compression is attained, additional tissue constriction can be obtained by rotating the ring element. As the ring element is rotated, the band element can be shortened. In this manner, adequate compression of the tissues can be accomplished. At this point, the tissue can be divided. If before cutting or based upon the intended application the operator wanted to remove the device, then this could be accomplished by having the operator put pressure on the pin element. This maneuver can result in the diameter of the pin element getting smaller and the space at, e.g., area 32 getting smaller. In this manner, the ring element can be released from the pin element.

In some cases, a device provided herein can be deployed in a manner that involves essentially human hands. To facilitate the use of the devices provided herein during, for example, medical and non-medical applications, specific tools can be used. For laparoscopic and robotic surgeries, a specialized deployment tool can be used. For example, with reference to FIG. 8, a deployment device 200 can include a handle 202 and a distal end region 204. In some cases, distal end region 204 can be configured to accommodate use with a trocar device (e.g., a 10 mm trocar). When used with a 10 mm trocar, a distal end region 204 can be 5 cm or less in length and can have a width between about 2 mm and about 5 mm. In some cases, depending on the application, the angle between distal end region 204 and handle 202 can be fixed or adjustable. Having an adjustable angle can allow the deployment device to be easily deployed. In some cases, the angle between distal end region 204 and handle 202 can be fixed at about 60°, 65°, 70°, 75°, 85°, 90°, 100°, 105°, 110°, 115°, 120°, or 125°.

Figure 8:
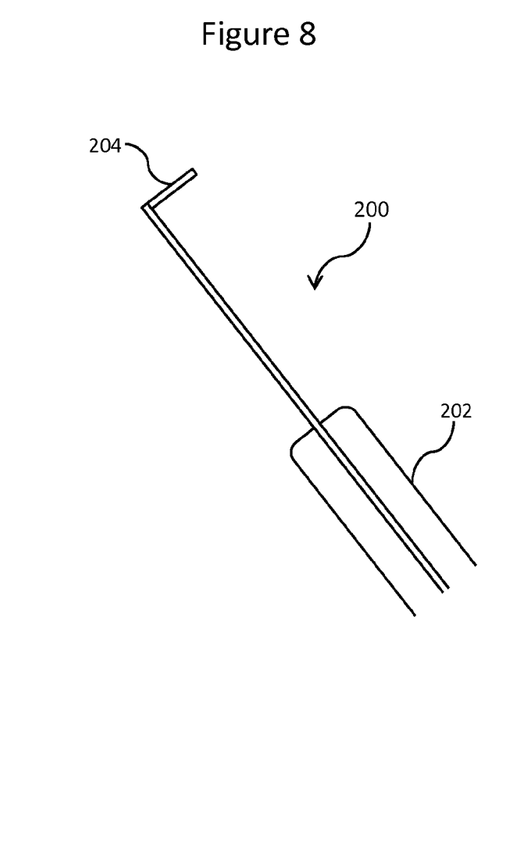
FIG. 8 is a side view of an exemplary deployment device.
Figure 9A:
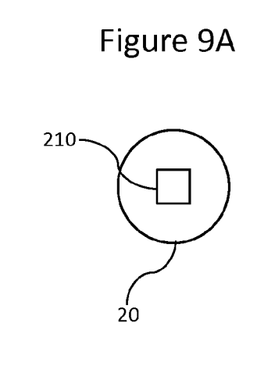
FIG. 9A is a side view of an exemplary proximal end region of a device provided herein.
Figure 9B:
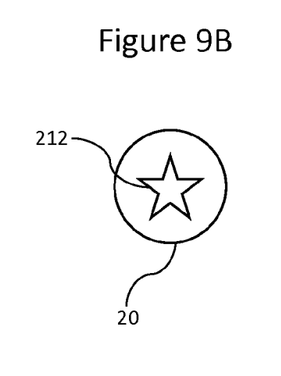
FIG. 9B is a side view of an exemplary proximal end region of a device provided herein.
Figure 10A:
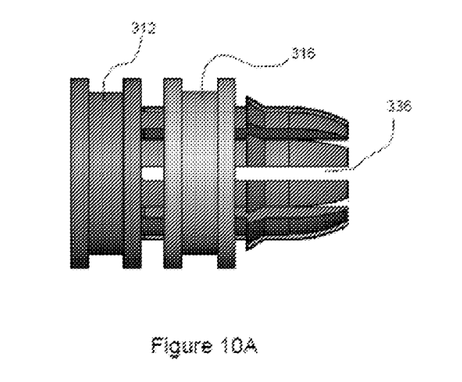
FIG. 10A is a side view of an exemplary device for fastening or constricting one or more items.
Figure 10B:
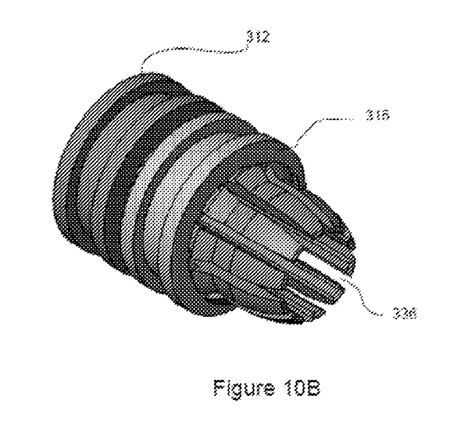
FIG. 10B is a prospective view of the device of FIG. 10A.
Figure 10C:
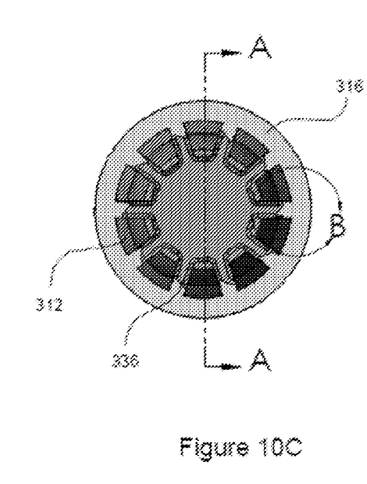
FIG. 10C is a front view of the device of FIG. 10A.
Figure 10D:
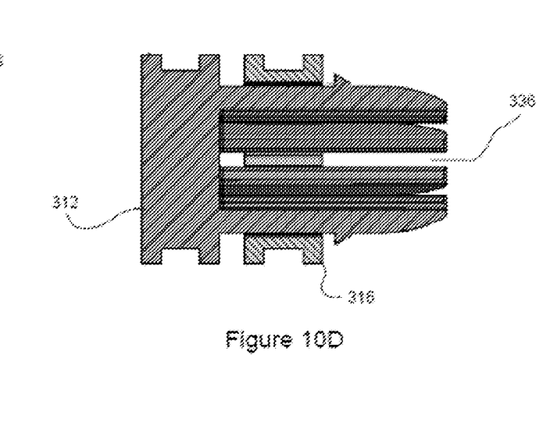
FIG. 10D is a cross section view of the device of FIG. 10A along the A-A line of FIG. 10C.
Figure 10E:
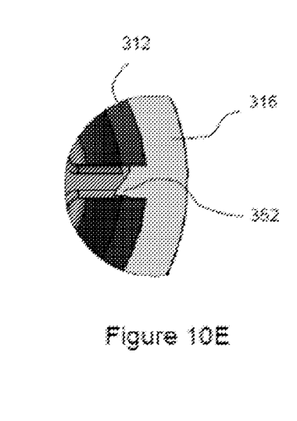
FIG. 10E is an enlarged view of the B-B region of FIG. 10C.

Deployment device 200 can be configured to attach releasably to a proximal end region of a pin element (e.g., proximal end region 20). For example, distal end region 204 can be shaped to engage releasably an opening within a proximal end region of a pin element (e.g., proximal end region 20). Examples of such opening include, without limitation, those shown in FIGS. 9A and 9B. In some cases, the opening or connection point of a proximal end region of a pin element can be a square shaped opening 210 as shown in FIG. 9A or can be a star shaped opening 212 as shown in FIG. 9B.

During use, a device provided herein (e.g., device 10) can be attached to a deployment device before being introduced into a mammal (e.g., an abdominal cavity of a human). In such cases, the device (e.g., device 10) can be held securely onto deployment device 200 during deployment through target tissue. In this situation, a distal end region (e.g., distal end region 204) can fit securely by, for example, gravity or friction into an opening at the proximal end region of the device (e.g., proximal end region 20 of device 10). After the deployment device is used to deploy the device (e.g., device 10), the deployment device can be backed away from the tissue, thereby releasing the device (e.g., device 10) from the deployment device.

Figures 14A, 14B, 14C:
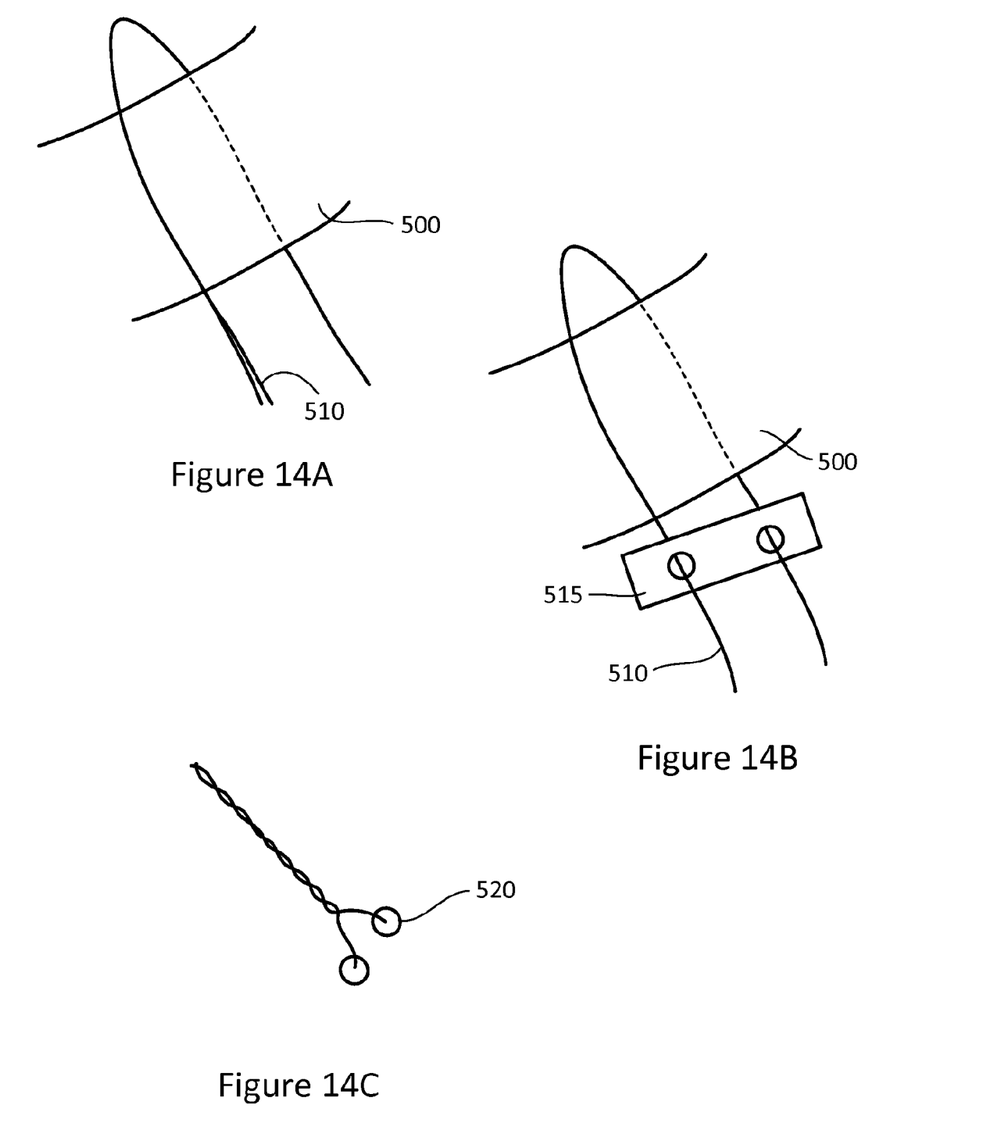
FIGS. 14A-C are prospective views of wires used to fasten or constrict one or more items (e.g., tissue within a body).

In some cases, one or more wires (e.g., silicon or polymer coated wires) can be used to fasten or constrict one or more items (e.g., tissue within a body). With reference to FIGS. 14A-C, wire 510 can be positioned about tissue 500. Wire 500 can be a coated wire such as a silicon coated wire. In some cases, multiple wires can be positioned about tissue 500. In such cases, the wires can be twisted to provide more stability. In some cases, the ends of the wire can be positioned through the holes of a plate or clip 515 (FIG. 14B). Plate or clip 515 can have two holes, one for each end of wire 510. In some cases, the ends of the wire can be twisted together to position or hold the tissue in a desired position. In some cases, the free ends of the wire can be inserted into or wrapped around a protection structure 520 (FIG. 14C). Protection structure 520 can be a ball or ball-like structure and can be made of any appropriate material such as silicon.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device comprising a pin element, a band element attached to said pin element, and a ring element attached to said band element, wherein said pin element comprises a shaft portion having a proximal end, a distal end, and an axis extending from said proximal end to said distal end, wherein said shaft portion comprises a locking structure and a protrusion, wherein said ring element is configured to be advanced over said distal end along said axis toward said proximal end and is configured to engage said locking structure, wherein said ring element is configured to rotate with respect to said pin element in a first direction, and wherein said ring element is configured to interact with said protrusion in a manner that restricts rotation of said ring element with respect to said pin element in a direction opposite said first direction, wherein said pin element is compressible, and wherein compression of said pin element releases said ring element from said locking structure such that said ring element is removable from said pin element.

2. The device of claim 1, wherein said pin element comprises a pointed distal end region.

3. The device of claim 1, wherein said pin element comprises a band holding region.

4. The device of claim 3, wherein said band holding region is at a proximal end region of said pin element.

5. The device of claim 1, wherein said pin element comprises two or more locking structures.

6. The device of claim 1, wherein said pin element comprises two or more protrusions.

7. The device of claim 1, wherein said pin element comprises a hollow central region along said axis.

8. The device of claim 1, wherein said pin element comprises a blunt distal end.

9. The device of claim 1, wherein said ring element comprises a continuous ring structure.

10. The device of claim 1, wherein said ring element comprises an inner surface comprising a ratcheting structure configured to engage said protrusions.

11. The device of claim 1, wherein said ring element comprises a band holding region.

12. The device of claim 1, wherein said band element comprises a protrusion.

13. The device of claim 12, wherein said protrusion of said band element is a spike-like structure.

14. The device of claim 1, wherein said band element comprises two or more protrusions.

15. A method for using a device to constrict vascular tissue, wherein said device comprises a pin element, a band element attached to said pin element, and a ring element attached to said band element, wherein said pin element comprises a shaft portion having a proximal end, a distal end, and an axis extending from said proximal end to said distal end, wherein said shaft portion comprises a locking structure and a protrusion, wherein said ring element is configured to be advanced over said distal end along said axis toward said proximal end and is configured to engage said locking structure, wherein said ring element is configured to rotate with respect to said pin element in a first direction, and wherein said ring element is configured to interact with said protrusion in a manner that restricts rotation of said ring element with respect to said pin element in a direction opposite said first direction, wherein said method comprises:

(a) positioning said pin element in proximity with said vascular tissue, (b) positioning said ring element around said vascular tissue such that said band element is positioned at least partially about said vascular tissue, (c) advancing said ring element over said distal end and along said axis toward said proximal end to a position wherein said ring element engages said locking structure and a closed loop is formed at least partially around said vascular tissue, and (d) rotating said ring element in said first direction to shorten the free length of said band element, thereby applying the desired amount of constriction to said vascular tissue.

16. The method of claim 15, wherein said pin element comprises a pointed distal end region.

17. The method of claim 15, wherein said pin element is compressible.

18. The method of claim 17, wherein compression of said pin element releases said ring element from said locking structure such that said ring element is removable from said pin element.

19. The method of claim 15, wherein said pin element comprises a band holding region.

20. The method of claim 19, wherein said band holding region is at a proximal end region of said pin element.

21. The method of claim 15, wherein said pin element comprises two or more locking structures.

22. The method of claim 15, wherein said pin element comprises two or more protrusions.

23. The method of claim 15, wherein said pin element comprises a hollow central region along said axis.

24. The method of claim 15, wherein said pin element comprises a blunt distal end.

25. The method of claim 15, wherein said ring element comprises a continuous ring structure.

26. The method of claim 15, wherein said ring element comprises an inner surface comprising a ratcheting structure configured to engage said protrusions.

27. The method of claim 15, wherein said ring element comprises a band holding region.

28. The method of claim 15, wherein said band element comprises a protrusion.

29. The method of claim 28, wherein said protrusion of said band element is a spike-like structure.

30. The method of claim 15, wherein said band element comprises two or more protrusions.

* * * * *